(12) United States Patent
Huang et al.

(10) Patent No.: US 10,911,059 B2
(45) Date of Patent: Feb. 2, 2021

(54) SIGNAL PROCESSING SYSTEM USING ANALOG-TO-DIGITAL CONVERTER WITH DIGITAL-TO-ANALOG CONVERTER CIRCUITS OPERATING IN DIFFERENT VOLTAGE DOMAINS AND EMPLOYING MISMATCH ERROR SHAPING TECHNIQUE AND ASSOCIATED SIGNAL PROCESSING METHOD

(71) Applicant: MEDIATEK INC., Hsin-Chu (TW)

(72) Inventors: Wei-Hsiang Huang, Hsin-Chu (TW); Yun-Shiang Shu, Hsin-Chu (TW); Su-Hao Wu, Hsin-Chu (TW)

(73) Assignee: MEDIATEK INC., Hsin-Chu (TW)

( * ) Notice: Subject to any disclaimer, the term of this patent is extended or adjusted under 35 U.S.C. 154(b) by 0 days.

(21) Appl. No.: 16/809,581

(22) Filed: Mar. 5, 2020

(65) Prior Publication Data
US 2020/0295772 A1    Sep. 17, 2020

Related U.S. Application Data

(60) Provisional application No. 62/817,665, filed on Mar. 13, 2019.

(51) Int. Cl.
*H03M 1/06* (2006.01)
*A61B 5/04* (2006.01)
*A61B 5/00* (2006.01)

(52) U.S. Cl.
CPC ....... *H03M 1/0626* (2013.01); *A61B 5/04017* (2013.01); *A61B 5/7225* (2013.01)

(58) Field of Classification Search
CPC . H03M 1/0626; A61B 5/7225; A61B 5/04017
(Continued)

(56) References Cited

U.S. PATENT DOCUMENTS 7,443,329 B2 * 10/2008 Sutardja ................ H03M 1/682
341/144
8,681,026 B2 * 3/2014 Xiao .................... H03M 1/1047
341/118

(Continued)

OTHER PUBLICATIONS

Shu, An Oversampling SAR ADC with DAC Mismatch Error Shaping Achieving 105dB SFDR and 101dB SNDR over 1kHz BW in 55nm CMOS, ISSCC 2016/ Session 27/ Hybrid and Nyquist Data Converters/ 27.2.

(Continued)

*Primary Examiner* — Lam T Mai
(74) *Attorney, Agent, or Firm* — Winston Hsu

(57) ABSTRACT

A signal processing system includes an analog-to-digital converter (ADC) that is used to convert a first analog value into a first digital value and convert a second analog value into a second digital value. The ADC includes a first digital-to-analog converter (DAC) circuit and a second DAC circuit operating in different voltage domains. A first bit segment and a second bit segment of each digital value are determined via the first DAC circuit and the second DAC circuit, respectively. An analog injection value is injected to the second analog value, the analog injection value is converted from a digital injection value formed by a subset of bits of the second bit segment of the first digital value, and the second bit segment of the second digital value is derived from injecting the digital injection value to a digital value determined by the second DAC circuit.

20 Claims, 8 Drawing Sheets

(58) Field of Classification Search
USPC .................................................. 341/118–155
See application file for complete search history.

(56) References Cited

U.S. PATENT DOCUMENTS

| | | | | |
|---|---|---|---|---|
| 9,774,345 | B1* | 9/2017 | Yoshioka | H03M 1/804 |
| 9,787,316 | B2 | 10/2017 | Shu | |
| 9,973,202 | B2* | 5/2018 | Yoshioka | H03M 1/462 |
| 10,116,323 | B2* | 10/2018 | Tsai | H03M 1/0626 |
| 10,284,213 | B2* | 5/2019 | Bandyopadhyay | H03M 1/0854 |
| 10,333,543 | B1* | 6/2019 | Hurrell | H03M 1/201 |
| 10,340,932 | B2* | 7/2019 | Bandyopadhyay | H03M 3/426 |
| 2006/0164276 | A1* | 7/2006 | Luh | H03M 1/0668 341/155 |
| 2007/0241950 | A1* | 10/2007 | Petilli | H03M 1/0663 341/143 |
| 2013/0194115 | A1* | 8/2013 | Wu | H03M 1/144 341/110 |
| 2013/0222162 | A1* | 8/2013 | Xiao | H03M 1/1047 341/120 |
| 2017/0077937 | A1* | 3/2017 | Shu | H03M 1/0673 |
| 2017/0230056 | A1* | 8/2017 | Shu | H03M 1/066 |
| 2017/0359081 | A1* | 12/2017 | Chen | H03M 1/468 |
| 2019/0149162 | A1* | 5/2019 | Lin | G01S 13/06 341/120 |

OTHER PUBLICATIONS

Michael Inerfield et al., An 11.5-ENOB 100-MS/s 8mW Dual-Reference SAR ADC in 28nm CMOS, 2014 Symposium on VLSI Circuits Digest of Technical Papers, 2014 IEEE, pp. 1-2, XP032622448, 2014.

Yun-Shiang Shu et al., An Oversampling SAR ADC With DAC Mismatch Error Shaping Achieving 105 dB SFDR and 101 dB SNDR Over 1 kHz BW in 55 nm CMOS, IEEE Journal of Solid-State Circuits, vol. 51, No. 12, Dec. 2016, 2016 IEEE, pp. 2928-2940, XP055716811.

Lin He et al., Self-Dithering Technique for High-Resolution SAR ADC Design, IEEE Transactions on Circuits and Systems-II: Express Briefs, vol. 62, No. 12, Dec. 2015, 2015 IEEE, pp. 1124-1128, XP011592534.

* cited by examiner

SIGNAL PROCESSING SYSTEM USING ANALOG-TO-DIGITAL CONVERTER WITH DIGITAL-TO-ANALOG CONVERTER CIRCUITS OPERATING IN DIFFERENT VOLTAGE DOMAINS AND EMPLOYING MISMATCH ERROR SHAPING TECHNIQUE AND ASSOCIATED SIGNAL PROCESSING METHOD

CROSS REFERENCE TO RELATED APPLICATIONS

This application claims the benefit of U.S. provisional application No. 62/817,665, filed on Mar. 13, 2019 and incorporated herein by reference.

BACKGROUND

The present invention relates to a system for conversion between an analog domain and a digital domain, and more particularly, to a signal processing system using an analog-to-digital converter (ADC) with digital-to-analog converter (DAC) circuits operating in different voltage domains and employing a mismatch error shaping (MES) technique.

A semiconductor circuitry system with functionality of conversion between digital and analog domains is essential for modern electronic devices, including a mobile phone, a notebook/tablet computer, a digital camera/camcorder, a navigation system, etc. Regarding a multi-channel application, one conventional signal processing chip design may employ multiple analog-to-digital converters (ADCs) for dealing with analog-to-digital conversion associated with analog signals of different channels. However, implementing multiple ADCs in a single chip increases the chip area inevitably. To reduce the chip area, another conventional signal processing chip design may adopt a time-multiplexing ADC that is shared between different channels in a time-multiplexing manner. However, if the time-multiplexing ADC is implemented by a delta-sigma ADC, the delta-sigma ADC and a following cascaded integrator-comb (CIC) filter both need to be reset during an interval between analog-to-digital conversion of analog signals of two channels. Since an effective sampling frequency is reduced due to the intermittent reset intervals, a large-sized anti-aliasing filter (AAF) preceding the delta-sigma ADC is needed by each channel to ensure the signal quality of an analog signal fed into the time-multiplexing delta-sigma ADC. As a result, the chip area cannot be effectively reduced due to the large-sized AAFs.

Thus, there is a need for an innovative signal processing chip design for a multi-channel application.

SUMMARY

One of the objectives of the claimed invention is to provide a signal processing system using an analog-to-digital converter (ADC) with digital-to-analog converter (DAC) circuits operating in different voltage domains and employing a mismatch error shaping (MES) technique.

According to a first aspect of the present invention, an exemplary signal processing system is disclosed. The exemplary signal processing system includes an analog-to-digital converter (ADC) that is arranged to convert a first analog value into a first digital value and convert a second analog value into a second digital value. The ADC includes a first digital-to-analog converter (DAC) circuit and a second DAC circuit with mismatch error shaping (MES). The first DAC circuit is arranged to operate in a first voltage domain that employs a first reference voltage, wherein a first bit segment of the first digital value and a first bit segment of the second digital value are determined via the first DAC circuit. The second DAC circuit is arranged to operate in a second voltage domain that employs a second reference voltage different from the first reference voltage, wherein a second bit segment of the first digital value and a second bit segment of the second digital value are determined via the second DAC circuit. An analog injection value is injected to the second analog value when the ADC is in operation for determining the second digital value, where the analog injection value is converted from a digital injection value formed by a subset of bits of the second bit segment of the first digital value, and the second bit segment of the second digital value is derived from injecting the digital injection value to a digital value determined by the second DAC circuit.

According to a second aspect of the present invention, an exemplary signal processing method is disclosed. The exemplary signal processing method includes: performing an analog-to-digital conversion to convert a first analog value into a first digital value and convert a second analog value into a second digital value, wherein the analog-to-digital conversion comprises: performing a first digital-to-analog conversion process in a first voltage domain that employs a first reference voltage, wherein a first bit segment of the first digital value and a first bit segment of the second digital value are determined via the first digital-to-analog conversion process; and performing a second digital-to-analog conversion process with mismatch error shaping (MES) in a second voltage domain that employs a second reference voltage different from the first reference voltage, wherein a second bit segment of the first digital value and a second bit segment of the second digital value are determined via the second digital-to-analog conversion process; and an analog injection value is injected to the second analog value when the analog-to-digital conversion is in operation for determining the second digital value, where the analog injection value is converted from a digital injection value formed by a subset of bits of the second bit segment of the first digital value, and the second bit segment of the second digital value is derived from injecting the digital injection value to a digital value determined by the second digital-to-analog conversion process.

These and other objectives of the present invention will no doubt become obvious to those of ordinary skill in the art after reading the following detailed description of the preferred embodiment that is illustrated in the various figures and drawings.

DETAILED DESCRIPTION

Certain terms are used throughout the following description and claims, which refer to particular components. As one skilled in the art will appreciate, electronic equipment manufacturers may refer to a component by different names. This document does not intend to distinguish between components that differ in name but not in function. In the following description and in the claims, the terms "include" and "comprise" are used in an open-ended fashion, and thus should be interpreted to mean "include, but not limited to . . . ". Also, the term "couple" is intended to mean either an indirect or direct electrical connection. Accordingly, if one device is coupled to another device, that connection may be through a direct electrical connection, or through an indirect electrical connection via other devices and connections.

For converting a digital input to an analog output, a digital-to-analog converter (DAC) selectively activates a subset of a plurality of conversion elements (e.g., resistors, capacitors or current sources, etc.) according to a digital value of the digital input, so as to synthesize the analog output. However, the conversion elements suffer deviations (e.g., variations) from their expected values, and therefore introduce mismatch error during conversion. Some kinds of analog-to-digital converters (ADCs) also adopt conversion elements and/or utilize internal DACs to perform analog-to-digital conversion. Therefore, suppressing mismatch error is important for both DAC and ADC. In some embodiments of the present invention, a mismatch error shaping (MES) technique is employed to mitigate a mismatch error resulting from capacitance mismatch and reference voltage mismatch.

Figure 1:
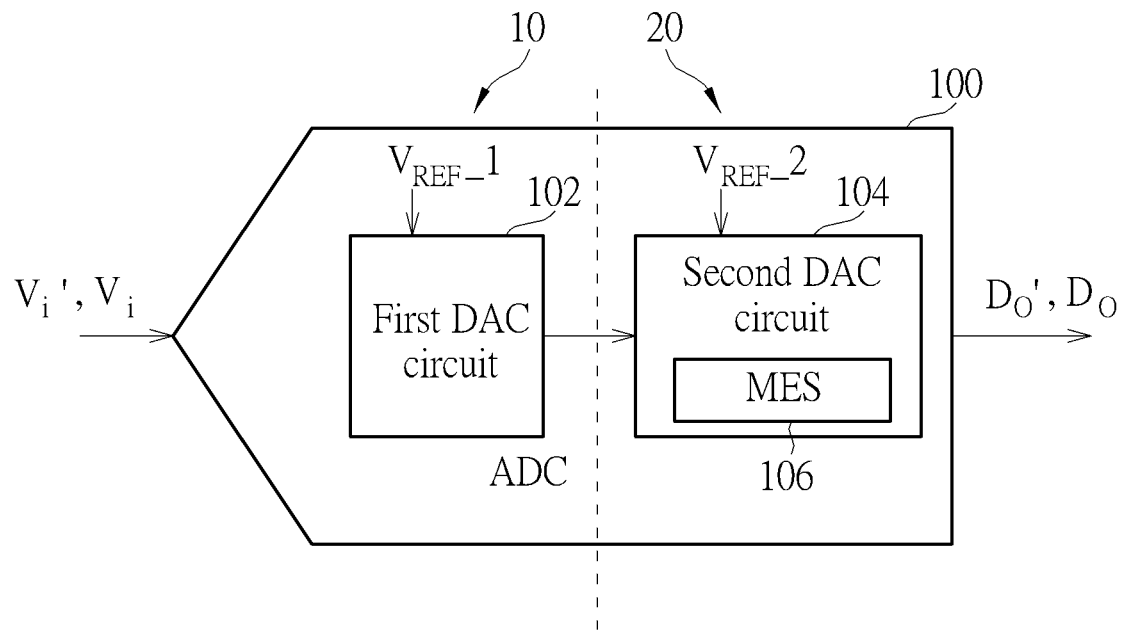
FIG. 1 is a diagram illustrating an analog-to-digital converter (ADC) with digital-to-analog converter (DAC) circuits operating in different voltage domains and employing a mismatch error shaping (MES) technique according to an embodiment of the present invention.

FIG. 1 is a diagram illustrating an analog-to-digital converter (ADC) with digital-to-analog converter (DAC) circuits operating in different voltage domains and employing a mismatch error shaping (MES) technique according to an embodiment of the present invention. The ADC 100 converts a first analog value Vi' (e.g., a previously sampled voltage level) into a first digital value Do' (e.g., a previous digital code), and converts a second analog value Vi (e.g., a currently sampled voltage level) into a second digital value Do (e.g., a current digital code). In this embodiment, the ADC 100 includes a first digital-to-analog converter (DAC) circuit 102, and further includes a second DAC circuit 104 with a mismatch error shaping scheme (denoted by "MES") 106 implemented therein. The first DAC circuit 102 is arranged to operate in a first voltage domain 10 that employs a first reference voltage $V_{REF\_1}$, where a first bit segment of the first digital value Do' and a first bit segment of the second digital value Do are determined via the first DAC circuit 102. The second DAC circuit 104 is arranged to operate in a second voltage domain 20 that employs a second reference voltage $V_{REF\_2}$ different from the first reference voltage $V_{REF\_1}$, where a second bit segment of the first digital value Do' and a second bit segment of the second digital value Do are determined via the second DAC circuit 104. For example, the first reference voltage $V_{REF\_1}$ may be higher than the second reference voltage $V_{REF\_2}$, transistors in the first DAC circuit 102 may be implemented using input/output (I/O) devices, and transistors in the second DAC circuit 104 may be implemented using core devices. For another example, the first bit segment may be a most significant bit (MSB) segment, the second bit segment may be a least significant bit (LSB) segment, the first DAC circuit 102 may be an MSB DAC, and the second DAC circuit 104 may be an LSB DAC.

In some embodiments of the present invention, the MES scheme 106 may be implemented using an MES technique disclosed in U.S. Pat. No. 9,787,316, entitled "SYSTEM FOR CONVERSION BETWEEN ANALOG DOMAIN AND DIGITAL DOMAIN WITH MISMATCH ERROR SHAPING". The instant application and the U.S. Pat. No. 9,787,316 are owned by the same assignee, and the sole inventor of the U.S. Pat. No. 9,787,316 is a co-author of the instant application. The entire contents of U.S. Pat. No. 9,787,316 are incorporated herein by reference.

In accordance with the MES scheme 106, an analog injection value is injected to the second analog value Vi when the ADC 100 is in operation for determining the second digital value Do, where the analog injection value is converted from a digital injection value formed by a subset of bits of the second bit segment of the first digital value Do', and the second bit segment of the second digital value Do is derived from injecting the digital injection value to a digital value determined by the second DAC circuit 104. Further details of the MES scheme 106 are described as below.

Figure 2:
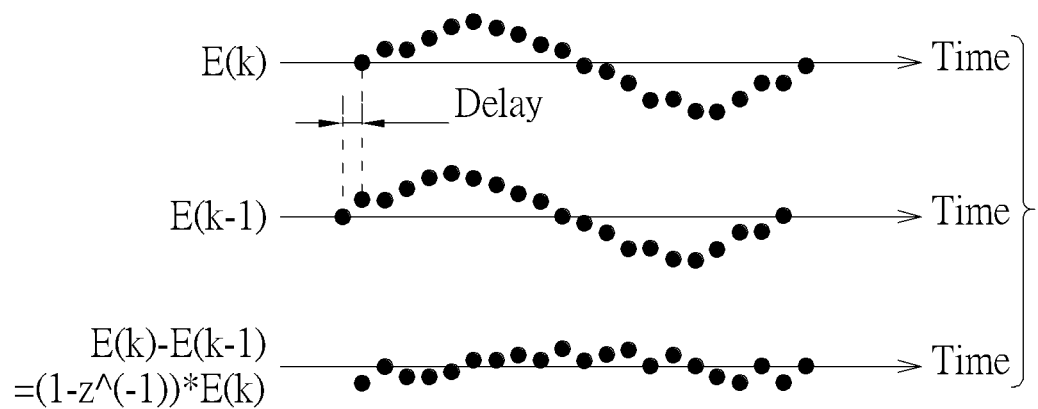
FIG. 2 is a diagram illustrating mismatch error shaping according to an embodiment of the invention.

Temporal filtering may be utilized to shaping mismatch error, such that the shaped mismatch error may distribute away from bands of desired signal. FIG. 2 is a diagram illustrating mismatch error shaping according to an embodiment of the invention. As shown in FIG. 2, mismatch error of converting a sequence of values may form an error sequence E(k) with k denoting time index, and the sequence E(k) may be slowly varying at frequencies near bands of desired signal, and hence contaminate desired signal (not shown). However, by subtracting a delayed sequence E(k−1) from the sequence E(k), the resultant sequence E(k)−E(k−1) may be fast varying at frequencies away from bands of desired signal. Thus, the mismatch error is shaped to a high-pass band. In terms of z-transform, the delayed sequence may also be expressed as $z^{-1}*E(k)$. Accordingly, the sequence E(k)−E(k−1) may be expressed as $(1-z^{-1})*E(k)$, meaning the error E(k) is filtered by a first-order high-pass filter $(1-z^{-1})$.

Figure 3:
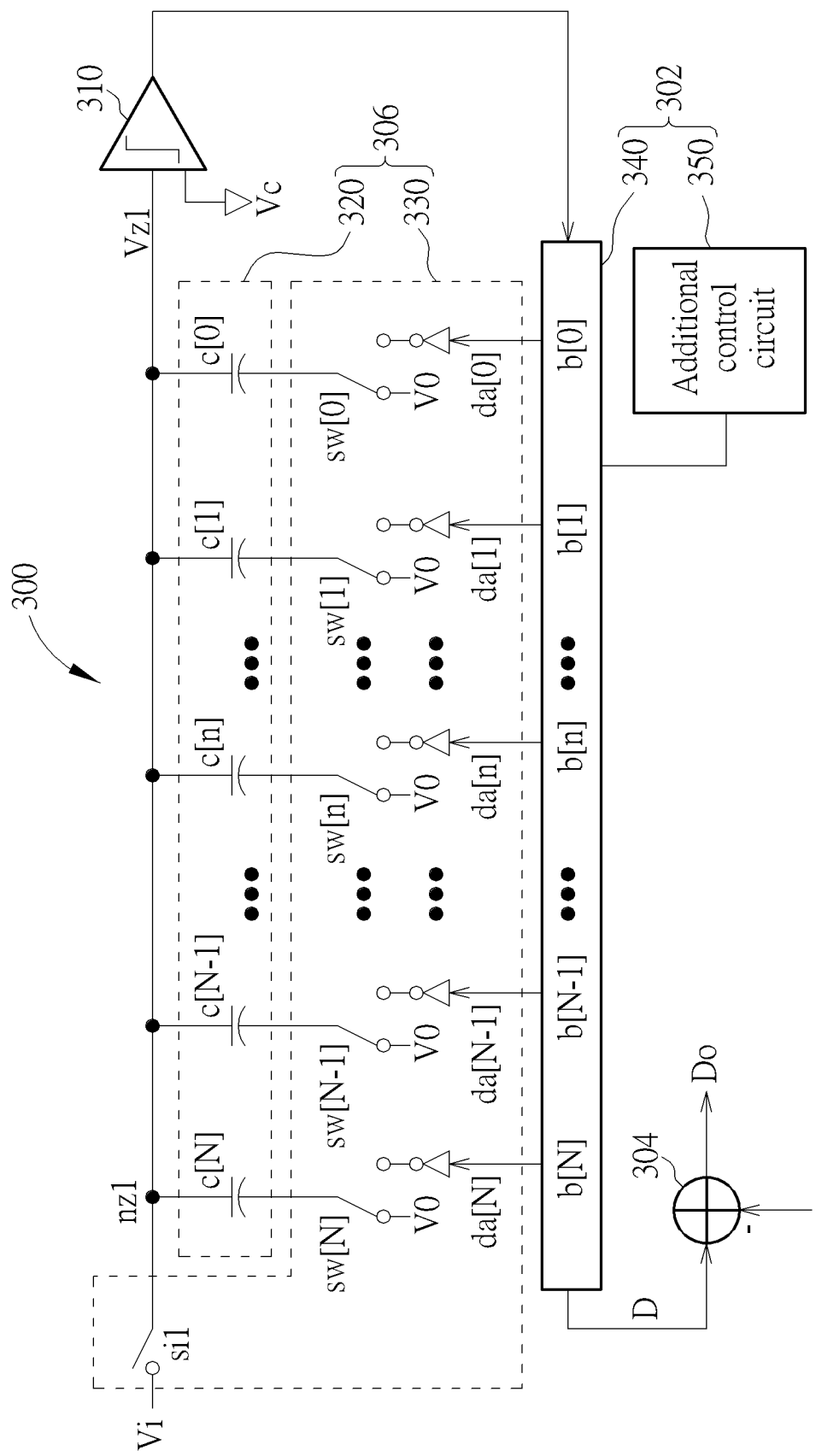
FIG. 3 is a diagram illustrating an ADC system according to an embodiment of the invention.

FIG. 3 is a diagram illustrating an ADC system according to an embodiment of the invention. The ADC 300 may implement a successive approximation (SAR) ADC for converting an analog value Vi to a digital value Do with MES. The ADC system 300 includes a comparator 310, a register 340, a peripheral circuit 330, an additional control circuit 350 and a capacitor array 320 which includes capacitors c[N], c[N−1], . . . , c[1], and c[0]. The peripheral circuit 330 may include a switch si1, a plurality of switches sw[N], sw[N−1], . . . , sw[1], and sw[0], and a plurality of bias circuits da[N], da[N−1], . . . , da[1], and da[0]. The switch si1 is coupled between the analog value Vi and a common node nz1. The comparator 310 is coupled to the node nz1, and is capable of checking if a voltage Vz1 at the node nz1 is greater than a voltage Vc. Each capacitor c[n] (for n=N, N−1, . . . , 1, 0) may have a top terminal coupled to the node nz1, and a bottom terminal coupled to the switch sw[n] to be selectively conducted to a constant reset voltage V0 (e.g., a ground level) or the bias circuit da[n]. The register 340 may register bits b[N], b[N−1], . . . , b[1], and b[0]. Each bias circuit da[n] may provide a voltage −b[n]*Vr according to the bit b[n], where Vr may be a reference voltage (e.g., supply voltage) used in a voltage domain. The ADC system 300 in FIG. 3 is a single-ended example, but can be extended to a differential design.

Figure 4:
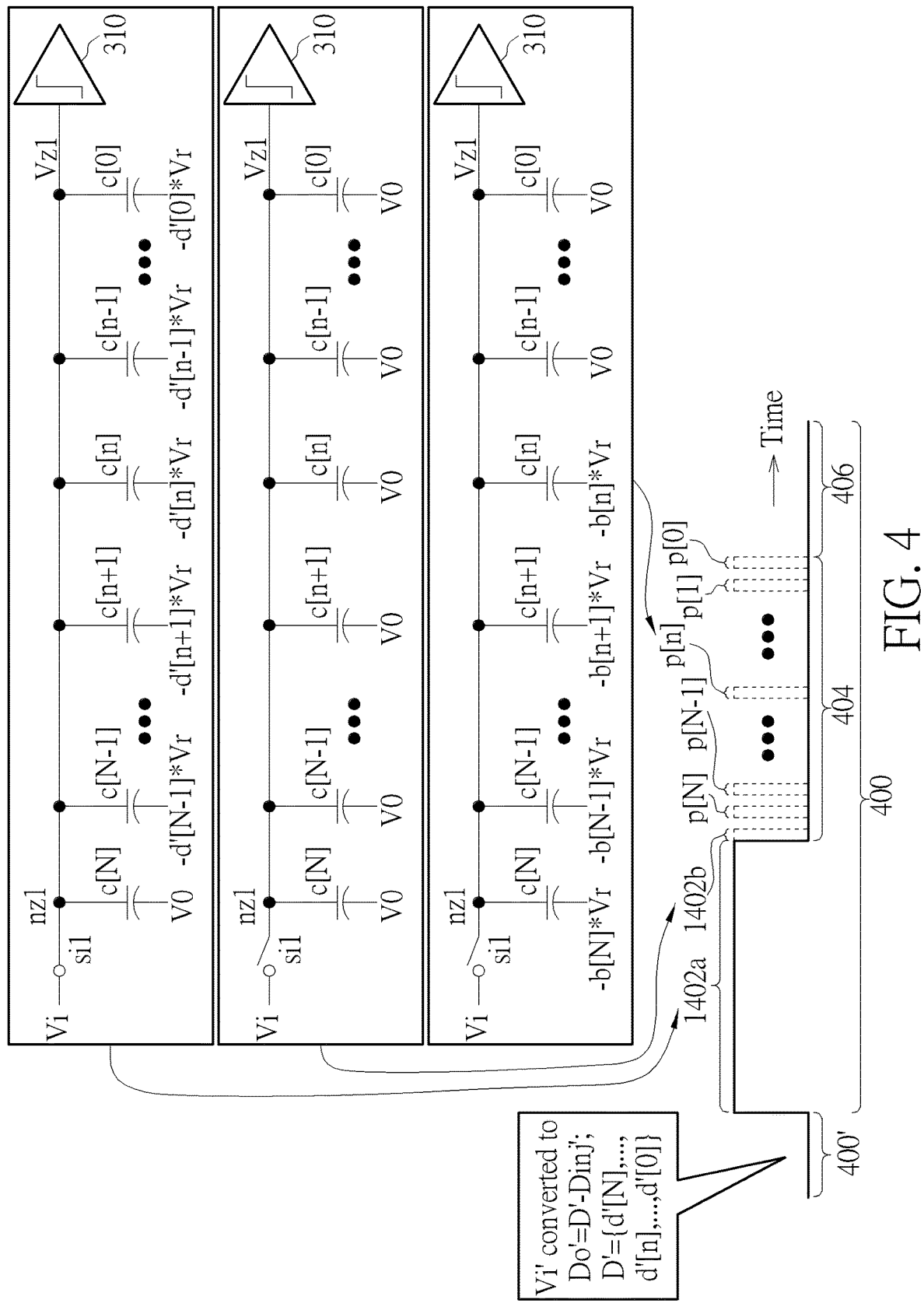
FIG. 4 illustrates operations of the ADC system shown in FIG. 3.

Please refer to FIG. 3 in conjunction with FIG. 4. FIG. 4 is a diagram illustrating operations of the ADC system 300 shown in FIG. 3. The ADC system 300 spends a cycle 400 to convert the analog value Vi to the digital value Do, as shown in FIG. 4. Before the cycle 400, during a previous cycle 400', the ADC system 300 has converted a previous analog value Vi' to a previous digital value Do'=D'−Dinj', with digital values D' and Dinj' respectively being previous versions of two digital values D and Dinj, and D'={d'[N], . . . , d'[n], . . . , d'[0]}.

The cycle 400 includes a sample-and-inject phase 402a, a reset phase 402b, a conversion phase 404 and an optional spare phase 406 (some designs may not have the spare phase). During the sample-and-injection phase 402a, the switch si1 conducts the analog value Vi to the node nz1, and the additional control circuit 350 controls the register 340 to keep registering the bits d'[N] to d'[0] as the bits b[N] to b[0], controls a first subset (e.g., sw[N]) of the switches sw[N] to sw[0] to conduct the voltage V0 to the bottom terminals of a first subset (e.g., c[N]) of the capacitors c[N] to c[0], and controls a second subset (e.g., sw[N−1] to sw[0]) of the switches sw[N] to sw[0] to respectively conduct a corresponding second subset (e.g., da[N−1] to da[0]) of the bias circuits da[N] to da[0] to the bottom terminals of a corresponding second subset (e.g., c[N−1] to c[0]) of the capacitors c[N] to c[1], such that each bias circuit da[n] belonging to the second subset of the bias circuits provides a voltage −d'[n]Vr to the bottom terminal of the capacitor c[n].

After the sample-and-injection phase 402a, the switch si1 stops conducting the analog value Vi to the node nz1, the additional control circuit 350 controls the peripheral circuit 330 to conduct the bottom terminals of the capacitors c[N] to c[0] to the voltage V0 during the reset phase 402b, and the bits b[N] to b[0] of the register 340 are reset to be undetermined. Thus, an analog injection value Vinj (not shown) reflecting a sum d[N−1]*c[N−1]+d[N−2]*c[N−2]+ . . . +d[1]*c[1]+ . . . +d[0]*c[0] is combined with the analog value Vi to form a combined analog value Vcb (not shown), and the combined analog value Vcb will be converted to a digital value at the comparison phase 404. In other words, as the capacitor array 320 and the peripheral circuit 330 jointly function as a DAC 306 during the comparison phase 404 by reflecting the digital bits b[N] to b[0] to the analog voltage Vz1, the additional control circuit 350 and the register 340 have jointly operated as a first injection circuit 302 for enabling the analog injection value Vinj to be injected to the voltage Vz1 during the sample-and-injection phase 402a and the reset phase 402b. The analog injection value Vinj is converted from the digital injection value Dinj by the DAC 306, wherein the digital injection value Dinj is formed by the second subset (e.g., d'[N−1] to d'[0]) of bits of the previous digital value D', e.g., Dinj={d'[N−1], . . . , d'[0]}.

During the comparison phase 404, the switch si1 stops conducting the analog value Vi to the node nz1. The comparison phase 404 includes a plurality of bit-decision periods p[N], p[N−1], . . . , p[1] and p[0]. After phase 402a and before the period pr[N], the comparator 310 determines whether the voltage Vz is greater than the voltage Vc to determine whether the bit b[N] is 1 or the opposite. During the period p[N], the switch sw[N] switches to the bias circuit da[N] which provides a setting voltage −b[N]*Vr, while the switches sw[N−1] to sw[0] remain conducting to the voltage V0, such that the voltage Vz1 at the node nz1 reflects a value Vcb−b[N]*Vr*c[N]/ct, with ct reflecting a total capacitance of the capacitors c[N] to c[0]. The comparator 310 determines whether the voltage Vz1 is greater than the voltage Vc to determine whether the bit b[N−1] is 1 or the opposite.

Once the bit b[N−1] is determined, the ADC system 300 proceeds to the period p[N−1]. During the period p[N−1], the switch sw[N−1] switches to the bias circuit da[N−1] which provides a voltage −b[N−1]*Vr, while the switches sw[N−2] to sw[0] remain conducting to the voltage V0, so the voltage Vz1 reflects a value Vcb−Vr*(b[N]*c[N]+b[N−1]c[N−1])/ct. The comparator 310 determines whether the voltage Vz1 is greater than the voltage Vc to determine whether the bit b[N−2] is 1 or the opposite.

As the bits b[N−1] to b[n] are successively determined respectively after the periods pr[N], pr[N−1], . . . , pr[n+1], at the period p[n], the switches sw[N] to sw[n] respectively switch to the bias circuits da[N] to da[n] which respectively provide voltages −b[N]*Vr to −b[n+1]*Vr and −b[n]*Vr, while the switches sw[n−1] to sw[0] remain conducting to the voltage V0, so the voltage Vz1 reflects a value Vcb−Vr*(b[N]*c[N]+b[N−1]*c[N−1]+ . . . +b[n+1]*c[n+1]+b[n]*c[n])/ct. The comparator 310 determines whether the voltage Vz1 is greater than the voltage Vc to determine whether the bit b[n−1] is 1 or the opposite. After the periods pr[N] to pr[0], all the bits b[N] to b[0] are determined to form the digital value D={b[N], . . . , b[n], . . . , b[0]}.

Practical capacitances of the capacitors c[N] to c[0] deviate from ideal capacitances. However, the register 340 and the additional control circuit 350 collectively operate as a first injection 302 enabling the analog injection value Vinj to be injected to the analog value Vcb during the phases 402a and 402b. Symmetrically in the digital domain, the ADC system 300 may, for example, further include a second injection circuit 304 (modeled as a sum block) for combining the digital value D with the digital injection value Dinj to form the digital value Do. Therefore, mismatch of the capacitor array 320 is shaped away from bands of desired signal.

According to the invention, absolute capacitance deviation of each individual capacitor c[n] is less essential than deviation of the relative capacitance ratio of the capacitors c[N] to c[0], because MES according to invention performs shaping symmetrically in both digital domain and analog domain. For example, assuming that the capacitor array includes capacitor c[3] to c[0] with ideal capacitance ratio 8:4:2:1 but actual capacitances 7.6, 4.3, 1.8 and 0.9 units. According to the invention, capacitance deviation of each capacitor is shaped by injecting corresponding deviations in both analog and digital domains, and the injections may be arranged to eliminate deviation defined by a selected capacitor, e.g., c[3], with deviations of the rest of capacitors left to be shaped. Hence, the selected capacitor c[3] may be considered to have a standard capacitance of 1 unit while the remaining capacitors c[2] to c[0] are considered to have relative capacitances 4.3/7.6, 1.8/7.6 and 0.9/7.6 units. Accordingly, in the embodiment of FIG. 3 and FIG. 4, the digital value Dinj injected in digital domain is formed by the second subset of bits (e.g., d'[N−1] to d'[0]) of the previous digital value D', not by all the bits d'[N] to d'[0]. For example, the digital value Dinj may equal d'[N−1]*$2^{(N-1)}$+ . . . +d'[0]*$2^0$, while the digital value D' equals d'[N]*$2^N$+d'[N−1]*$2^{(N-1)}$+ . . . +d'[0]*$2^0$.

Figure 5:
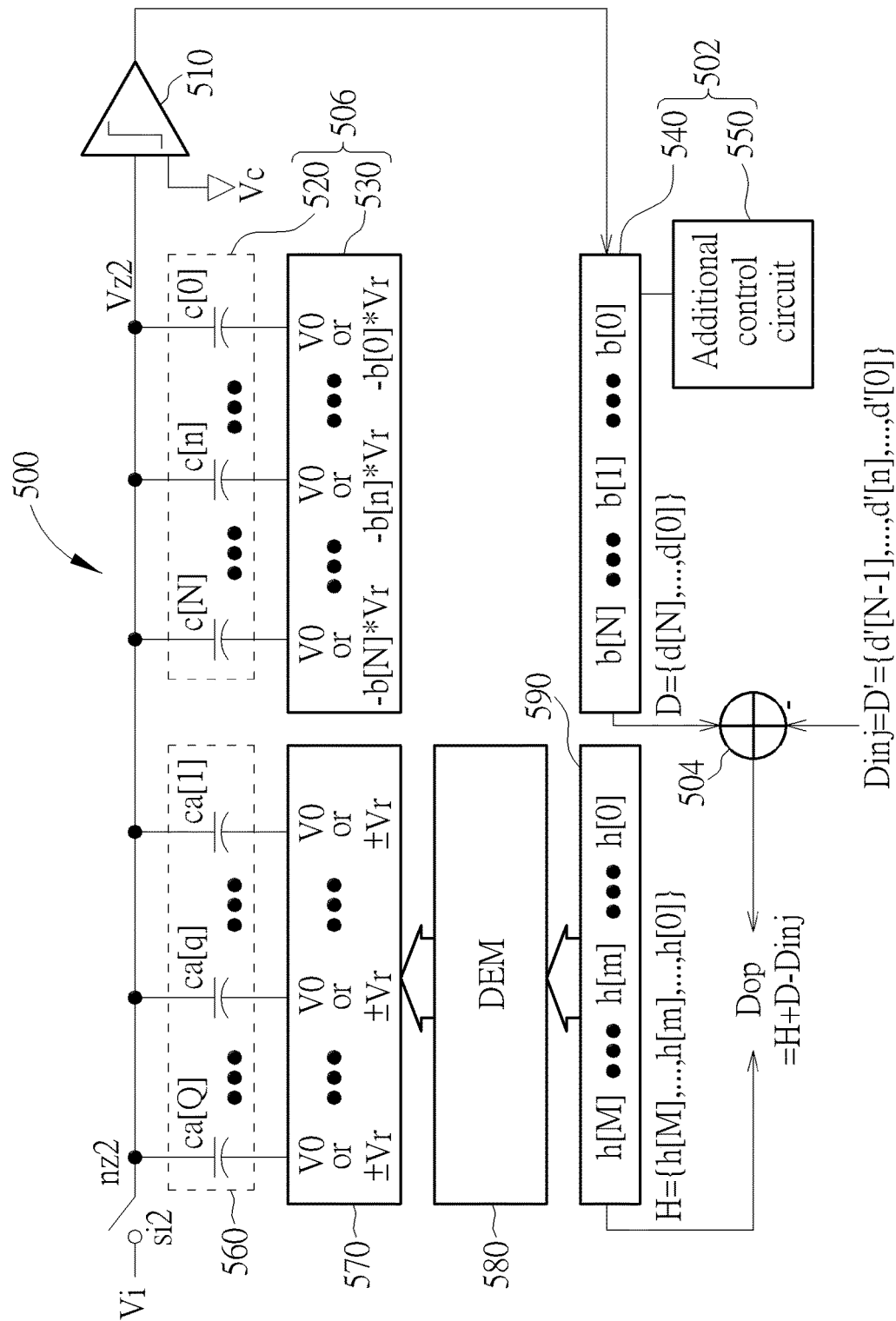
FIG. 5 is a diagram illustrating another ADC system according to an embodiment of the invention.
Figure 6:
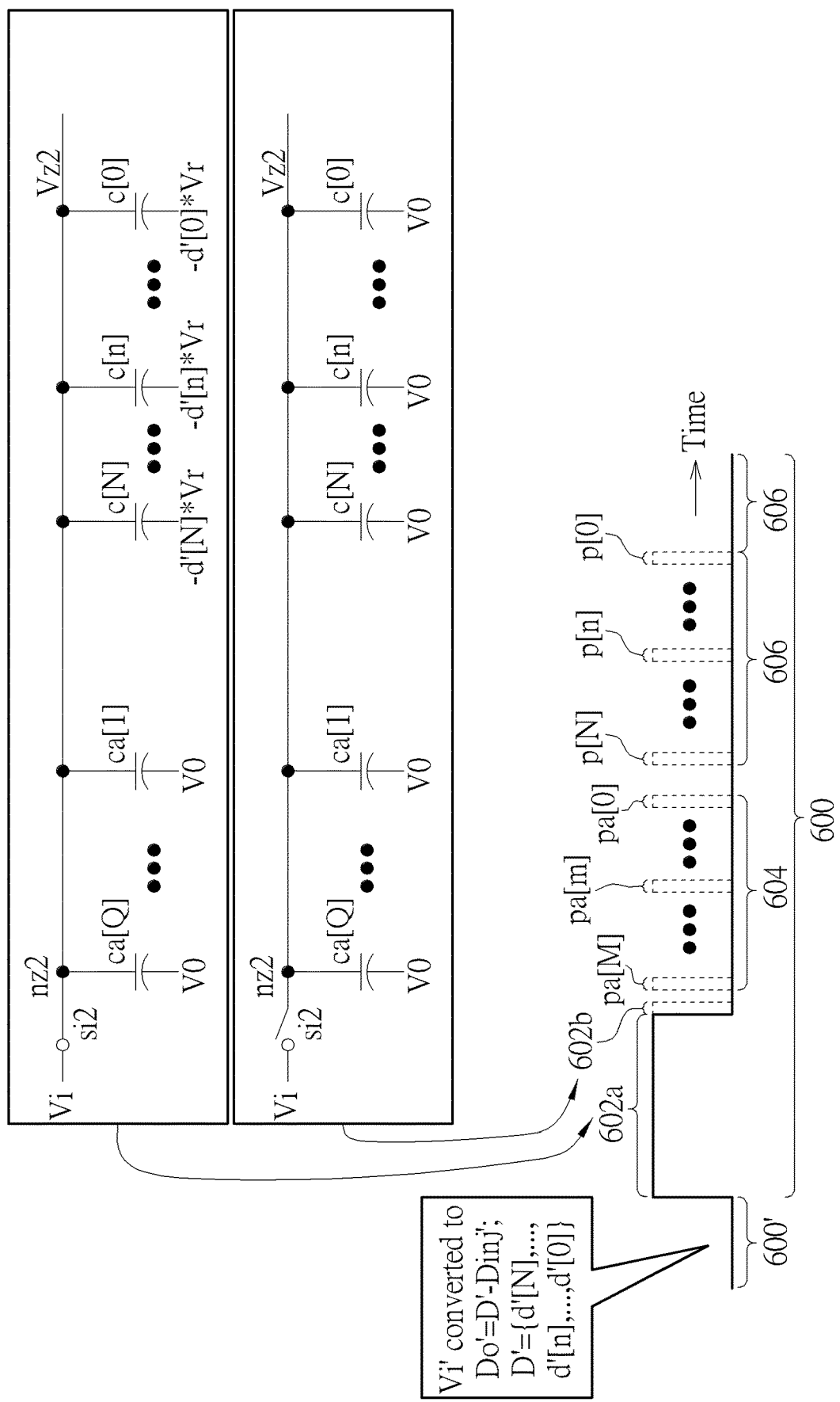
FIG. 6 and FIG. 7 illustrate operations of the ADC system shown in FIG. 5.
Figure 7:
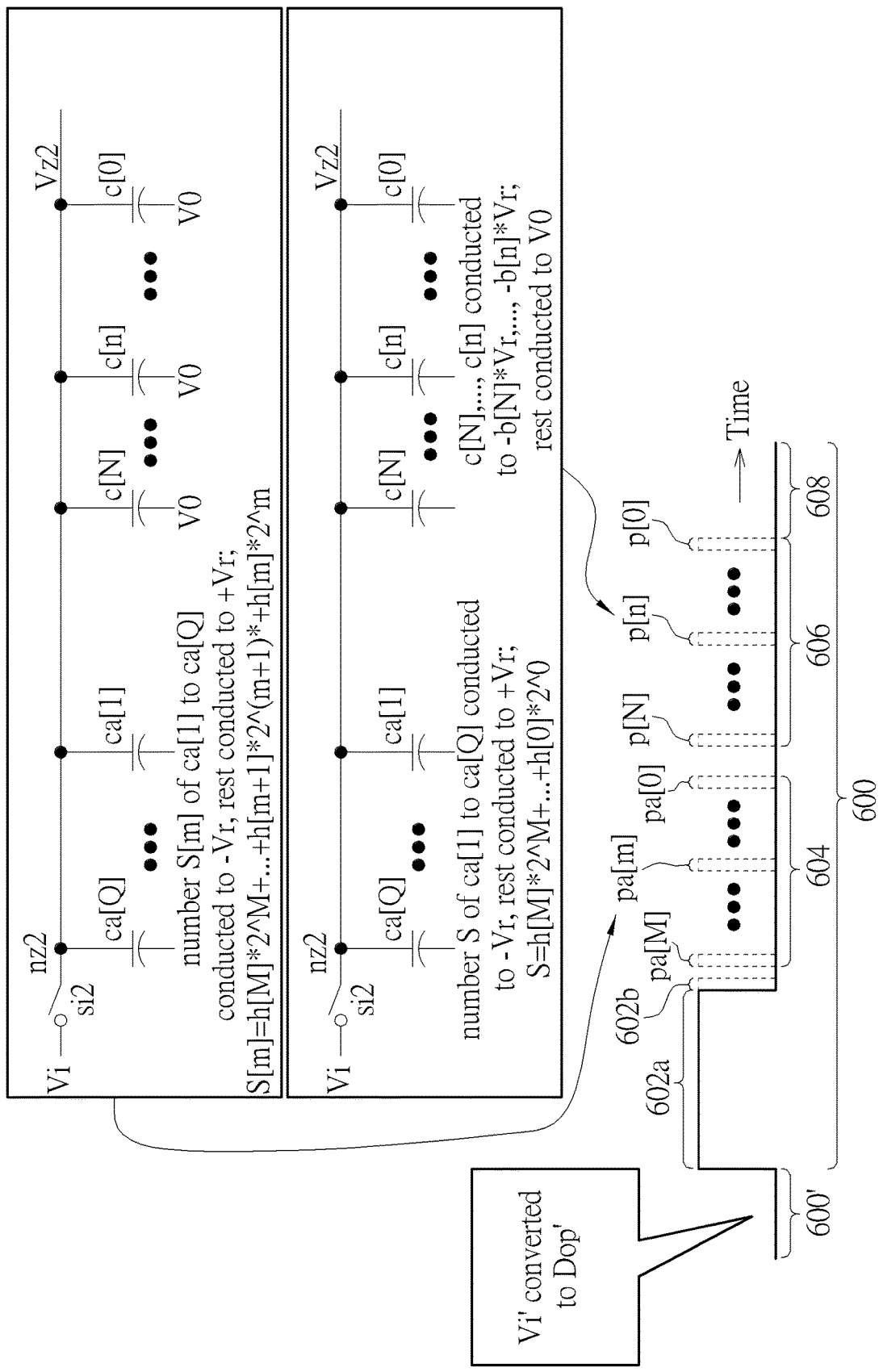

Please refer to FIG. 5 in conjunction with FIG. 6 and FIG. 7. FIG. 5 illustrates another ADC system according to an embodiment of the invention. FIG. 6 and FIG. 7 illustrate operations of the ADC system 500 shown in FIG. 5. The ADC system 500 may implement a SAR ADC for converting an analog value Vi to a digital value Dop. The digital value Dop is formed by combining two digital values H and D as well as a digital injection value Dinj with a minus sign, where the digital value H equals {h[M], . . . , h[m], . . . , h[0]}, and the digital value D equals {d[N], . . . , d[n], . . . , d[0]}.

The ADC system 500 includes a switch sit, a comparator 510, two registers 540 and 590, two peripheral circuits 530 and 570, an additional control circuit 550, a dynamic element matching (DEM) circuit 580 and two capacitor arrays 520 and 560. The switch sit is coupled between the analog value Vi and a common node nz2. The comparator 510 is coupled to the node nz2, and is capable of determining if a voltage Vz2 at the node nz2 is greater than a voltage Vc.

The capacitor array 520 includes capacitors c[N], . . . , c[n], . . . , c[0]; each capacitor c[n] (for n=N, N−1, . . . , 0) has a top terminal coupled to the node nz2, and a bottom terminal coupled to the peripheral circuit 530. The register 540 is coupled to the peripheral circuit 530, and registers bits b[N] to b[0]. The peripheral circuit 530 selectively conducts the bottom terminal of each capacitors c[n] to a reset voltage V0 or a voltage −b[n]*Vr according to the bit b[n] of the register 540, where Vr may be a reference voltage (e.g., supply voltage) used in a voltage domain. The additional control circuit 550 is coupled to the register 540 and the peripheral circuit 530.

The capacitor array 560 includes a number Q of capacitors ca[Q], . . . , ca[q], . . . , ca[1]; each capacitor ca[q] (for q=Q, . . . , 1) has a top terminal coupled to the node nz2, and a bottom terminal coupled to the peripheral circuit 570. The number Q equals $2^{(M+1)}-1$. The DEM circuit 580 is coupled between the peripheral circuit 570 and the register 590. The register 590 registers bits h[M] to h[0] to form the digital value H. The DEM circuit 580 selects a number (one, some or all) of the capacitors ca[Q] to ca[1] by pseudo-random shuffling with the number reflecting the bits h[M] to h[0], and the peripheral circuit 570 conducts the bottom terminals of the selected capacitors to a voltage −Vr, and conducts the rest of the capacitors ca[Q] to ca[1] to a voltage +Vr. For example, the DEM circuit 580 codes a digital value represented by at least a portion (i.e., part or all) of bits h[M] to h[0] from binary code to thermometer code, and selects a number of the capacitors ca[Q] to ca[1] according to a determined thermometer code. Ideally, all the capacitors ca[Q] to ca[1] in the capacitor array 560 are equally weighted and the capacitors c[N] to c[0] are binary weighted. For example, an ideal ratio of capacitances of the capacitors ca[Q], . . . , ca[q], . . . , ca[1], c[N], . . . , c[n], . . . , c[0] is $2^{(N+1)}: \ldots : 2^{(N+1)}: \ldots : 2^{(N+1)}: 2^N: \ldots : 2^n: \ldots : 2^0$.

As shown in FIG. 6 and FIG. 7, the ADC system 500 spends a cycle 600 to convert the analog value Vi to the digital value Dop. Before the cycle 600, by a previous cycle 600', the ADC system 500 has converted a previous analog value Vi' to a previous digital value Dop'=H'+D'−Dinj', with H', D' and Dinj' being previous versions of the digital values H, D and Dinj, and D' equal to {d'[N], . . . , d'[0]}

The cycle 600 includes a sample-and-inject phase 602a, a reset phase 602b, an MSB conversion phase 604, an LSB conversion phase 606, and an optional spare phase 608 (some designs may not have the spare phase). During the sample-and-injection phase 602a (FIG. 6), the switch sit conducts the analog value Vi to the node nz2, and the additional control circuit 550 controls the register 540 to keep registering the bits d'[N] to d'[0] as the bits b[N] to b[0], and controls the peripheral circuit 530 for conducting the bottom terminals of the capacitors c[N] to c[0] respectively to the voltages −d[N]*Vr to −d[0]*Vr, where Vr may be a reference voltage (e.g., supply voltage) used in a voltage domain. During the sample-and-injection phase 602a, the peripheral circuit 570 keeps conducting the bottom terminals of the capacitors ca[Q] to ca[1] to the voltage V0, and the bits h[M] to h[0] of the register 590 are reset to be undetermined.

After the sample-and-injection phase 602a, the switch sit stops conducting the analog value Vi to the node nz2. During the reset phase 602b, the additional control circuit 550 controls the peripheral circuit 530 for conducting the bottom terminals of the capacitors c[N] to c[0] to the voltage V0, and the bits b[N] to b[0] of the register 540 are reset to be undetermined. Thus, an analog injection value Vinj (not shown) reflecting a sum d'[N]*c[N]*+. . . +d[0]*c[0] is combined with the analog value Vi to form a combined analog value Vcb (not shown) at the sample-and-inject phase 602a and the reset phase 602b, and the combined analog value Vcb will be converted to a digital value at the MSB and LSB comparison phases 604 and 606. As the capacitor array 520 and the peripheral circuit 530 collectively operate as a DAC 506 during the LSB comparison phase 604 by reflecting the digital bits b[N] to b[0] to the analog voltage Vz2, the register 540 and the additional control circuit 550 have collectively operated as a first injection circuit 502 for enabling the analog injection value Vinj to be injected to the voltage Vz2 during the sample-and-inject phase 602a and the reset phase 602b, with the analog injection value Vinj converted from a digital injection value Dinj=$D^1$={d'[N−1], . . . , d'[n], . . . , d'[0]} by the DAC 506.

After the sample-and-inject phase 602a and the reset phase 602b, the MSB comparison phase 604 starts, which includes a plurality of bit-decision periods pa[M], . . . , pa[m], . . . , pa[0]. After the phase 602b and before the period pa[M], the comparator 510 determines whether the voltage Vz2 is greater than the voltage Vc to determine whether the bit h[M] is 1 or the opposite. During the period pa[M], the DEM circuit 580 selects a number $h[M]*2^M$ of capacitors from the capacitors ca[Q] to ca[1] of the capacitor array 560, the peripheral circuit 570 conducts the bottom terminals of the selected $h[M]*2^M$ capacitors to the voltage −Vr and keeps conducting the bottom terminals of the rest unselected capacitors to the voltage +Vr, and the comparator 510 determines whether the voltage Vz2 is greater than the voltage Vc to determine whether the bit h[M−1] is 1 or the opposite, where Vr may be a reference voltage (e.g., supply voltage) used in a voltage domain. On the other hand, the peripheral circuit 530 keeps the bottom terminals of the capacitors c[N] to c[0] conducted to the voltage V0 during the MSB comparison phase 604.

During the period pa[m] (for m=(M−1) to 1, FIG. 7), the DEM circuit 580 selects a number S[m] of capacitors from the capacitors ca[Q] to ca[1] of the capacitor array 560, the peripheral circuit 570 conducts the bottom terminals of the selected S[m] capacitors to the voltage −Vr and keeps conducting the bottom terminals of the unselected (Q−S[m]) capacitors to the voltage +Vr, and the comparator 510 determines whether the voltage Vz2 is greater than the voltage Vc to determine if the bit h[m−1] equals 1. The number S[m] equals $h[M]*2^M+ \ldots +h[m+1]*2^{(m+1)}+h[m]*2^m$.

After the MSB comparison phase 604, the bits h[M] to h[0] are determined to form the most significant M+1 bits of the digital value Dop (i.e., an MSB segment of the digital value), and then the ADC system 500 proceeds to the LSB comparison phase 606. The comparison phase 606 includes a plurality of bit-decision periods p[N], ..., p[n], ..., p[0]. After phase 604 and before the period p[N], the comparator 510 determines whether the voltage Vz2 is greater than the voltage Vc to determine whether the bit b[N] is 1 or the opposite. During the period p[N], the peripheral circuit 530 conducts the bottom terminal of the capacitor c[N] to a voltage −b[n]*Vr and keeps conducting the bottom terminals of the capacitors c[N−1] to c[0] to the voltage V0, and the comparator 510 determines whether the voltage Vz2 is greater than the voltage Vc to determine whether the bit b[N−1] equals 1, where Vr may be a reference voltage (e.g., supply voltage) used in a voltage domain. On the other hand, after the MSB comparison phase 604, the peripheral circuit 570 conducts the bottom terminals of a number S of the capacitors ca[Q] to ca[1] to the voltage −Vr, and the conducts the bottom terminal of the remaining number (Q−S) of the capacitors ca[Q] to ca[1] to the voltage +Vr. The number S equals $h[M]*2^M + ... + h[0]*2^0$.

During the period p[n] (n=(N−2) to 1), the peripheral circuit 530 conducts the bottom terminals of the capacitors c[N] to c[n] respectively to the voltages −b[N]*Vr to −b[n]*Vr, and conducts the bottom terminal of the rest of capacitors c[n−1] to c[0] to the voltage V0. The comparator 510 determines whether the voltage Vz2 is greater than the voltage Vc to determine if the bit d[n−1] equals 1. After the LSB comparison phase 606, all the bits b[N] to b[0] are determined to form a digital value D={b[N], ..., b[n], ..., b[0]}. The ADC system 500 may, for example, further include a second injection circuit 504 (modeled as a sum block) for combining the digital value D and the digital injection value Dinj=D', and the combined result is further combined with the digital value H to form the digital value Dop. Therefore, by cooperation of the injection circuits 502 and 504, mismatch of the capacitor array 520 is shaped away from bands of desired signal. In addition, mismatch of the capacitor array 560 is shaped by operation of the DEM circuit 580, which shuffles usages of the capacitors ca[Q] to ca[1] for shaping their mismatches. Though DEM is also a technique for shaping mismatch, MES by symmetrically injections in digital and analog domains according to the invention is proved to be superior.

The aforementioned MES technique may be employed by the MES scheme 106 used by the ADC 100 with DAC circuits operating in different voltage domains. Specifically, the aforementioned MES technique is extended from shaping a mismatch error resulting from capacitor mismatch to shaping a mismatch error resulting from capacitor mismatch and reference voltage mismatch. Since charge mismatch may be regarded as a product of capacitor mismatch and reference voltage mismatch, the aforementioned MES technique may be employed for mitigating a charge mismatch error in a band of interest. For example, the ADC 100 may be built on the basis of the ADC system 500 shown in FIG. 5, where the capacitor array 560 and the peripheral circuit 570 collectively operate as an MSB DAC, the capacitor array 520 and the peripheral circuit 530 collectively operate as an LSB DAC, and a reference voltage Vr used by the MSB DAC is different from (e.g., higher than) a reference voltage Vr used by the LSB DAC.

Figure 8:
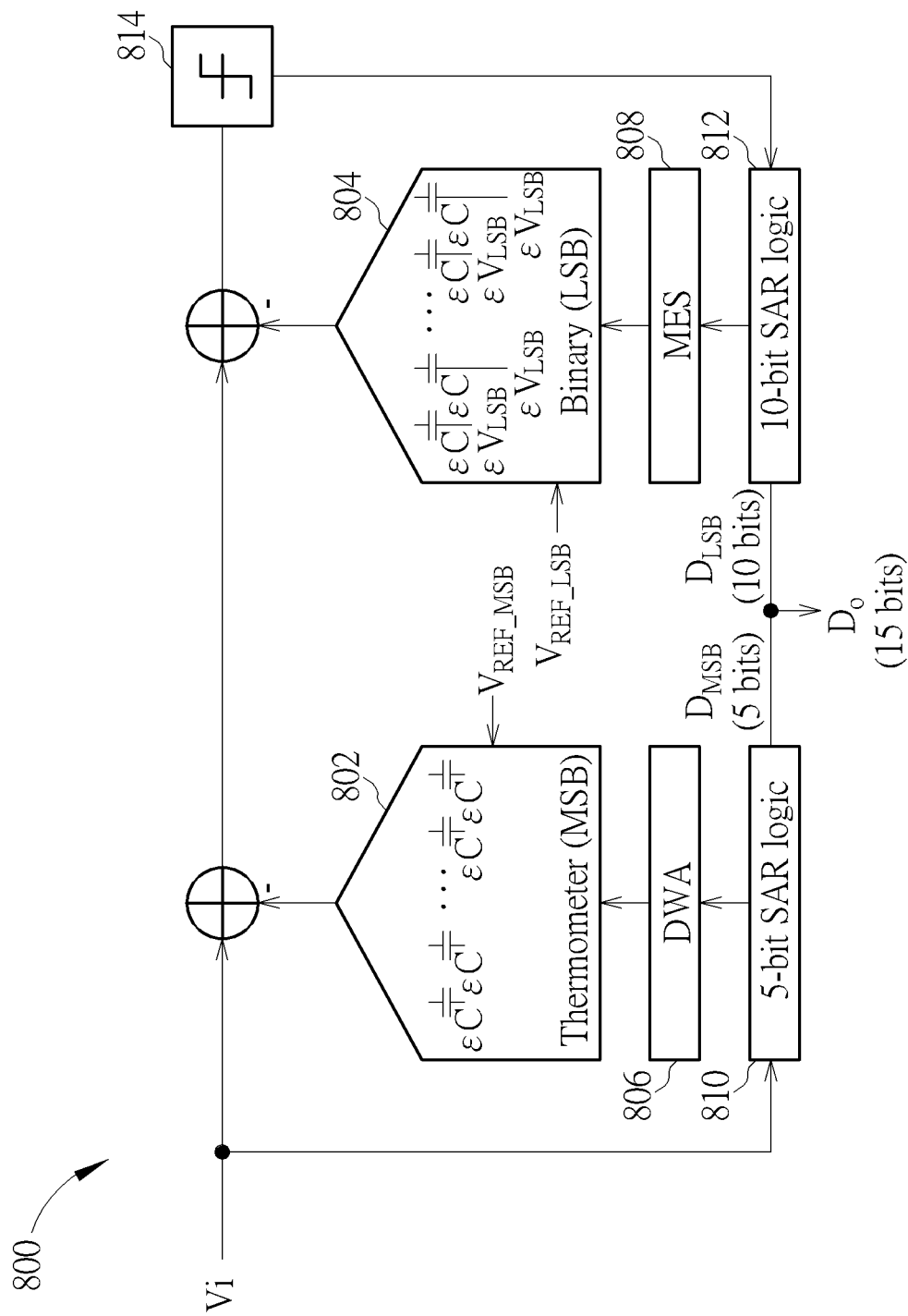
FIG. 8 is a diagram illustrating an example of an ADC with DAC circuits operating in different voltage domains and employing an MES technique according to an embodiment of the present invention.

FIG. 8 is a diagram illustrating an example of an ADC with DAC circuits operating in different voltage domains and employing an MES technique according to an embodiment of the present invention. The ADC 100 shown in FIG. 1 may be implemented using the ADC 800 shown in FIG. 8. In this embodiment, the ADC 800 is used to convert an analog value Vi into a 15-bit digital value Do, where the 15-bit digital value Do consists of a 5-bit MSB segment DMSB and a 10-bit LSB segment $D_{LSB}$. The ADC 800 includes an MSB DAC 802 operating under a first reference voltage $V_{REF\_MSB}$ (e.g., 2V) and an LSB DAC 804 operating under a second reference voltage $V_{REF\_LSB}$ (e.g., 1.2V), where the MSB DAC 802 is controlled by a 5-bit SAR logic circuit 810 through a data weighted averaging (DWA) scheme 806 (which is one of the simplest DEM schemes), and the LSB DAC 804 is controlled by a 5-bit SAR logic circuit 812 through an MES scheme 808. The fist DAC circuit 102 shown in FIG. 1 may be implemented by a combination of MSB DAC 802, DWA scheme 806, and 5-bit SAR logic circuit 810, where the first reference voltage $V_{REF\_1}$ is set by $V_{REF\_MSB}$. The second DAC circuit 104 shown in FIG. 1 may be implemented by a combination of LSB DAC 804, MES scheme 808, and 10-bit SAR logic circuit 812, where the second reference voltage $V_{REF\_2}$ is set by $V_{REF\_LSB}$. During an MSB comparison phase, bits of the 5-bit MSB segment DMSB are determined according to successive comparison results at a comparator 814. During an LSB comparison phase, bits of the 10-bit LSB segment $D_{LSB}$ are successively determined according to successive comparison results at the comparator 814.

Suppose that the ADC 800 uses a single capacitor array consisting of equally weighted capacitors implemented in the MSB DAC 802 and binary weighted capacitors implemented in the LSB DAC 802. The charge Q[n] contributed by applying a reference voltage $V_{REF}$ (which is either $V_{REF\_MSB}$ or $V_{REF\_LSB}$) to the capacitor C[n] (which is one capacitor of the single capacitor array) may be expressed using the following formula.

$$Q[n]=C[n]*V_{REF} \quad (1)$$

Hence, the voltage V[n] contributed to the analog value Vi may be expressed using the following formula.

$$V[n]=C[n]*V_{REF}/C_{total} \quad (2)$$

In above formula (2), $C_{total}$ represents a total capacitance of the single capacitor array. Hence, the voltage V[n] is proportional to C[n]*VREF. The mismatch error for the 10-bit LSB segment can be modeled as $\varepsilon V_{LSB}*\varepsilon C[9:0]$. With the help of the MES scheme 808, Do=$(D_{MSB}+D_{LSB})-z^{(-1)}*D_{LSB}$. Hence, the capacitor mismatch and the reference voltage mismatch can be filtered by one $1^{st}$ order high-pass filter $(1-z^{-1})$.

Figure 9:
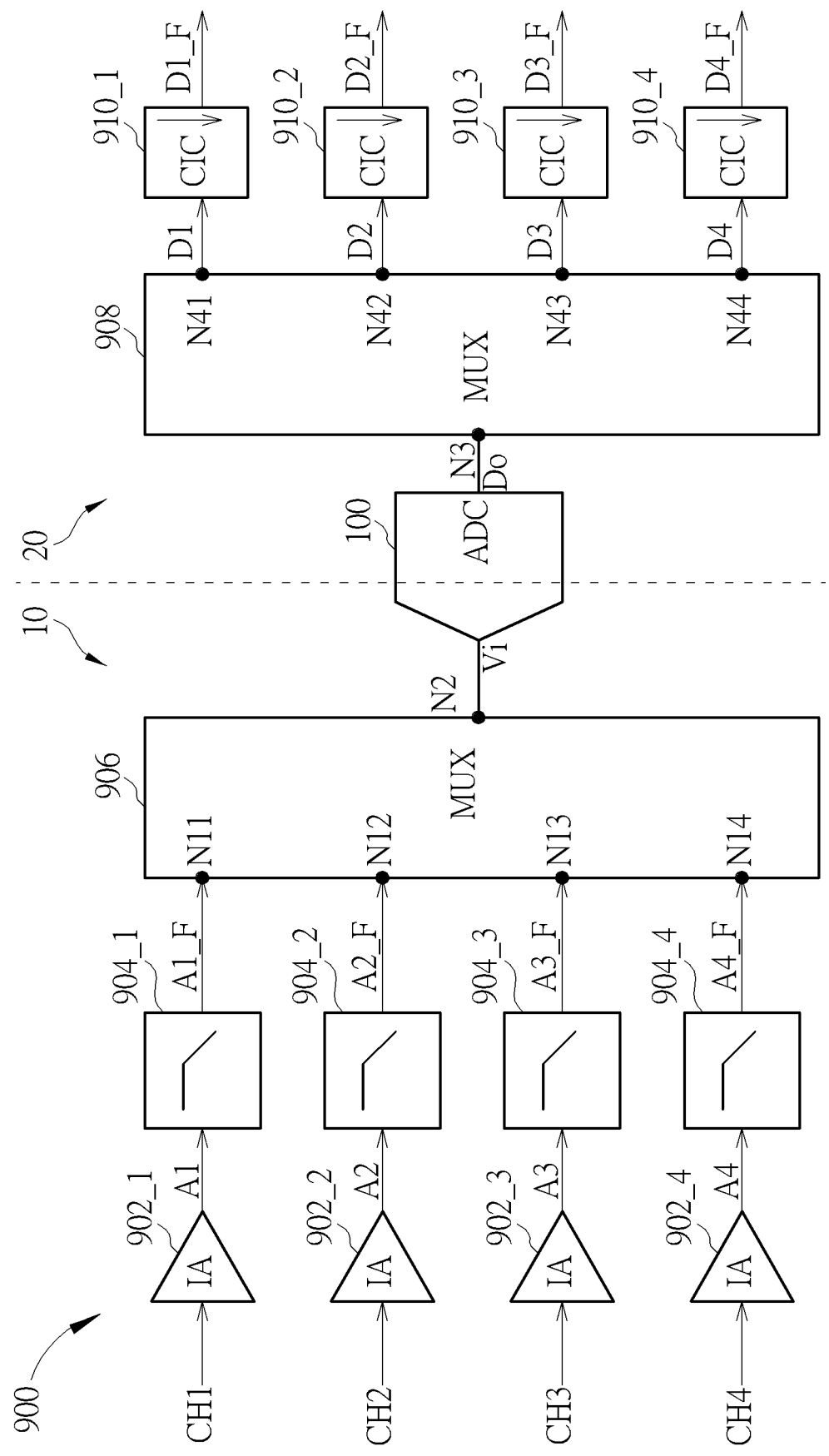
FIG. 9 is a diagram illustrating a signal processing system according to an embodiment of the present invention.

The ADC 100 with DAC circuits operating in different voltage domains and employing an MES technique can be employed by a multi-channel system for achieving a high ADC resolution and a low ADC area. FIG. 9 is a diagram illustrating a signal processing system according to an embodiment of the present invention. By way of example, but not limitation, the signal processing system 900 may be a part of an electrocardiography (ECG) system, and may be used to convert a multi-channel analog input of a wearable ECG analog front-end (AFE) into a multi-channel digital output for further diagnosis processing. In this embodiment, the signal processing system 900 is a four-channel system, including the aforementioned ADC 100 shown in FIG. 1 and further including a plurality of instrumentation amplifiers (IAs) 902_1, 902_2, 902_3, 902_4, a plurality of pre-processing filters such as anti-aliasing filters (AAFs) 904_1, 904_2, 904_3, 904_4, a plurality of multiplexing circuits (each denoted by "MUX") 906, 908, and a plurality of post-processing filters such as cascaded integrator-comb (CIC) filters 910_1, 910_2, 910_3, 910_4.

The instrumentation amplifiers 902_1-902_4 are arranged to generate analog signals A1, A2, A3, A4 of different channels CH1, CH2, CH3, CH4 to the anti-aliasing filters 904_1-904_4, respectively. The anti-aliasing filters 904_1-904_4 are arranged to applying filtering to analog signals A1-A4 of different channels CH1-CH4 and generate a plurality of filtered analog signals A1_F, A2_F, A3_F, A4_F, respectively. The multiplexing circuit 906 has a plurality of input ports N11, N12, N13, N14 and an output port N2, where the input ports N11-N14 are coupled to the anti-aliasing filters 904_1-904_4, respectively, and the output port N2 is coupled to the ADC 100. The multiplexing circuit 906 is arranged to output one of the filtered analog signals A1_F-A4_F as an analog input (e.g., analog value Vi) of the ADC 100. The cascaded integrator-comb filters 910_1-910_4 are arranged to apply filtering to a plurality of digital signals D1, D2, D3, D4 of different channels CH1-CH4 and generate a plurality of filtered digital signals D1 _F, D2_F, D3_F, D4_F, respectively. The multiplexing circuit 908 has an input port N3 and a plurality of output ports N41, N42, N43, N44, where the input port N3 is coupled to the ADC 100, and the output ports N41-N44 are coupled to the cascaded integrator-comb filters 910_1-910_4, respectively. The multiplexing circuit 908 is arranged to set one of the digital signals D1-D4 by a digital output (e.g., digital value Do) of the ADC 100.

The ADC 100 is shared among preceding anti-aliasing filters 904_1-904_4 in a time-multiplexing manner, and is shared among following cascaded integrator-comb filters 910_1-910_4 in a time-multiplexing manner. For example, during a first time slot allocated to the first channel CH1, the ADC 100 receives the filtered analog signal A1_F from the anti-aliasing filter 904_1 and generates the digital signal D1 to the cascaded integrator-comb filter 910_1; during a second time slot allocated to the second channel CH2, the ADC 100 receives the filtered analog signal A2_F from the anti-aliasing filter 904_2 and generates the digital signal D2 to the cascaded integrator-comb filter 910_2; during a third time slot allocated to the third channel CH3, the ADC 100 receives the filtered analog signal A3_F from the anti-aliasing filter 904_3 and generates the digital signal D3 to the cascaded integrator-comb filter 910_3; and during a fourth time slot allocated to the fourth channel CH4, the ADC 100 receives the filtered analog signal A4_F from the anti-aliasing filter 904_4 and generates the digital signal D4 to the cascaded integrator-comb filter 910_4.

The ADC 100 employed by the signal processing system 900 may be implemented using the ADC 800 shown in FIG. 8, where the ADC 800 may be built on the basis of the ADC system 500 shown in FIG. 5. Regarding a multi-channel application, N sets of registers (e.g., N sets of D-type flip flops) may be used to record DWA and MES results, the DWA scheme 806 may delay a 5-bit pointer for N cycles, and the MES scheme 808 may delay the 10-bit LSB segment $D_{LSB}$ for N cycles, where N is the number of multiplexed channels.

The reference voltage $V_{REF\_MSB}$ may be an ECG AFE supply voltage (e.g., 2V), and the reference voltage $V_{REF\_LSB}$ may be a digital supply voltage (e.g., 1.2V). In this embodiment, transistors used in the MSB DAC 802 may be implemented using I/O devices for dealing with an MSB comparison phase of an analog input with a large voltage swing (e.g., 4V). The transistors used in the LSB DAC 804 may be implemented using core devices for reducing the power consumption. In addition, the LSB DAC 804 can be used to increase the resolution of the ADC 100. The linearity of the ADC 100 may be degraded due to the MSB DAC 802 and the LSB DAC 804 operating under different reference voltages. To address this issue, the MES scheme 808 is implemented to mitigate a mismatch error resulting from capacitor mismatch and reference voltage mismatch. With the help of the MES scheme 808, no extra digital calibration engine is needed. Moreover, compared to a time-multiplexing delta-sigma ADC followed by only a single cascaded integrator-comb filter, the proposed time-multiplexing SAR ADC is followed by multiple cascaded integrator-comb filters through a multiplexing circuit, such that there is no need to reset the time-multiplexing SAR ADC and any cascaded integrator-comb filter during an interval between analog-to-digital conversion of analog signals of two channels. In this way, the anti-aliasing filtering requirement can be relaxed, thereby allowing small-sized anti-aliasing filters to be used by the signal processing system 900. To put it simply, the proposed time-multiplexing SAR ADC design has small ADC area, high resolution, and good linearity.

In above embodiments, the ADC 100 with DAC circuits operating in different voltage domains and employing an MES technique is built on the basis of SAR ADC architecture. However, this is for illustrative purposes only, and is not meant to be a limitation of the present invention. Alternatively, the ADC 100 can be implemented using any ADC architecture that is not the delta-sigma ADC architecture. For example, the ADC 100 with DAC circuits operating in different voltage domains and employing an MES technique may be built on the basis of flash ADC architecture. For another example, the ADC 100 with DAC circuits operating in different voltage domains and employing an MES technique may be built on the basis of pipelined ADC architecture.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:
1. A signal processing system comprising:
an analog-to-digital converter (ADC), arranged to convert a first analog value into a first digital value and convert a second analog value into a second digital value, wherein the ADC comprises:
a first digital-to-analog converter (DAC) circuit, arranged to operate in a first voltage domain that employs a first reference voltage, wherein a first bit segment of the first digital value and a first bit segment of the second digital value are determined via the first DAC circuit; and
a second DAC circuit with mismatch error shaping (MES), arranged to operate in a second voltage domain that employs a second reference voltage different from the first reference voltage, wherein a second bit segment of the first digital value and a second bit segment of the second digital value are determined via the second DAC circuit; and an analog injection value is injected to the second analog value when the ADC is in operation for determining the second digital value, where the analog injection value is converted from a digital injection value formed by a subset of bits of the second bit segment of the first digital value, and the second bit segment of the second digital value is derived from injecting the digital injection value to a digital value determined by the second DAC circuit.

2. The signal processing system of claim 1, wherein the ADC is a successive approximation (SAR) ADC.

3. The signal processing system of claim 2, wherein said MES is arranged to mitigate a mismatch error in a band of interest, where the mismatch error results from capacitor mismatch and reference voltage mismatch.

4. The signal processing system of claim 1, wherein the first bit segment of each of the first digital value and the second digital value is a most significant bit (MSB) segment, and the second bit segment of each of the first digital value and the second digital value is a least significant bit (LSB) segment.

5. The signal processing system of claim 1, wherein the first reference voltage is higher than the second reference voltage.

6. The signal processing system of claim 1, further comprising:
a plurality of first filters, arranged to apply filtering to a plurality of analog signals of different channels and generate a plurality of filtered analog signals, respectively;
a first multiplexing circuit, having a plurality of input ports and an output port, wherein the input ports are coupled to the first filters, respectively, the output port is coupled to the ADC, and the first multiplexing circuit is arranged to output one of the filtered analog signals as an analog input of the ADC;
a plurality of second filters, arranged to apply filtering to a plurality of digital signals of said different channels and generate a plurality of filtered digital signals, respectively; and
a second multiplexing circuit, having an input port and a plurality of output ports, wherein the input port is coupled to the ADC, the output ports are coupled to the second filters, respectively, and the second multiplexing circuit is arranged to set one of the digital signals by a digital output of the ADC.

7. The signal processing system of claim 6, wherein each of the first filters is an anti-aliasing filter (AAF).

8. The signal processing system of claim 6, wherein each of the second filters is a cascaded integrator-comb (CIC) filter.

9. The signal processing system of claim 6, further comprising:
a plurality of instrumentation amplifiers, arranged to generate the analog signals of said different channels to the first filters, respectively.

10. The signal processing system of claim 6, wherein the signal processing system is a part of an electrocardiography (ECG) system.

11. A signal processing method comprising:
performing an analog-to-digital conversion to convert a first analog value into a first digital value and convert a second analog value into a second digital value, wherein the analog-to-digital conversion comprises:
performing a first digital-to-analog conversion process in a first voltage domain that employs a first reference voltage, wherein a first bit segment of the first digital value and a first bit segment of the second digital value are determined via the first digital-to-analog conversion process; and
performing a second digital-to-analog conversion process with mismatch error shaping (MES) in a second voltage domain that employs a second reference voltage different from the first reference voltage, wherein a second bit segment of the first digital value and a second bit segment of the second digital value are determined via the second digital-to-analog conversion process; and an analog injection value is injected to the second analog value when the analog-to-digital conversion is in operation for determining the second digital value, where the analog injection value is converted from a digital injection value formed by a subset of bits of the second bit segment of the first digital value, and the second bit segment of the second digital value is derived from injecting the digital injection value to a digital value determined by the second digital-to-analog conversion process.

12. The signal processing method of claim 11, wherein the analog-to-digital conversion is a successive approximation (SAR) analog-to-digital conversion.

13. The signal processing method of claim 12, wherein said MES mitigates a mismatch error in a band of interest, where the mismatch error results from capacitor mismatch and reference voltage mismatch.

14. The signal processing method of claim 11, wherein the first bit segment of each of the first digital value and the second digital value is a most significant bit (MSB) segment, and the second bit segment of each of the first digital value and the second digital value is a least significant bit (LSB) segment.

15. The signal processing method of claim 11, wherein the first reference voltage is higher than the second reference voltage.

16. The signal processing method of claim 11, further comprising:
applying first filtering to a plurality of analog signals of different channels and generating a plurality of filtered analog signals, respectively;
selectively using one of the filtered analog signals as an analog input of the analog-to-digital conversion;
applying second filtering to a plurality of digital signals of said different channels and generating a plurality of filtered digital signals, respectively; and
selectively setting one of the digital signals by a digital output of the analog-to-digital conversion.

17. The signal processing method of claim 16, wherein said first filtering applied to each of the analog signals is performed by one anti-aliasing filter (AAF).

18. The signal processing method of claim 16, wherein said second filter applied to each of the digital signals is performed by one cascaded integrator-comb (CIC) filter.

19. The signal processing method of claim 16, further comprising:
generating, by a plurality of instrumentation amplifiers, the analog signals of said different channels to the first filters, respectively.

20. The signal processing method of claim 16, wherein the signal processing method is employed by an electrocardiography (ECG) system.

* * * * *